(12) United States Patent
Thompson et al.

(10) Patent No.: US 9,440,942 B2
(45) Date of Patent: *Sep. 13, 2016

(54) CHROMAN-DERIVED ANTI-ANDROGENS FOR TREATMENT OF ANDROGEN MEDIATED DISORDERS

(71) Applicant: Wisconsin Alumni Research Foundation, Madison, WI (US)

(72) Inventors: Todd A. Thompson, Madison, WI (US); George Wilding, Verona, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,942

(22) Filed: Jul. 10, 2014

(65) Prior Publication Data

US 2014/0323560 A1 Oct. 30, 2014

Related U.S. Application Data

(63) Continuation of application No. 13/966,775, filed on Aug. 14, 2013, now Pat. No. 8,809,387, which is a continuation of application No. 13/542,432, filed on Jul. 5, 2012, now Pat. No. 8,536,219, which is a continuation of application No. 12/581,501, filed on Oct. 19, 2009, now abandoned, which is a continuation of application No. 10/789,835, filed on Feb. 27, 2004, now Pat. No. 7,709,525.

(60) Provisional application No. 60/450,510, filed on Feb. 27, 2003.

(51) Int. Cl.
*A61K 31/353* (2006.01)
*C07D 311/72* (2006.01)

(52) U.S. Cl.
CPC ........... *C07D 311/72* (2013.01); *A61K 31/353* (2013.01)

(58) Field of Classification Search
CPC .................................................... A61K 31/353
See application file for complete search history.

(56) References Cited

U.S. PATENT DOCUMENTS

| | | | | |
|---|---|---|---|---|
| 6,174,864 B1 * | 1/2001 | Yoshikawa | .......... | A61K 31/353 514/27 |
| 6,242,479 B1 * | 6/2001 | Wechter | .............. | A61K 31/355 514/456 |
| 7,709,525 B2 * | 5/2010 | Thompson | ............ | C07D 311/72 514/456 |
| 7,863,324 B2 * | 1/2011 | Thompson | ............ | C07D 311/72 514/456 |
| 8,536,219 B2 * | 9/2013 | Thompson | ............ | C07D 311/72 514/456 |
| 8,809,387 B2 * | 8/2014 | Thompson | ............ | C07D 311/72 514/456 |

OTHER PUBLICATIONS

Bakalova et al. Acta Physiol. Pharmacol. Bulg., 2000, vol. 25, pp. 19-26.*
Hsiao et al. British Journal of Haematology, Jun. 1, 2002, vol. 117, pp. 699-704.*
Skinner et al. J. Med. Chem., 1967, vol. 10, No. 4, pp. 657-661.*
Sheu et al. Life Sciences, 1999, vol. 65, No. 2, pp. 197-206.*
Grundman Am. J. Clin. Nutr., 2000, vol. 71 (suppl.), pp. 630S-636S.*

* cited by examiner

*Primary Examiner* — James D Anderson
(74) *Attorney, Agent, or Firm* — Boyle Fredrickson, S.C.

(57) ABSTRACT

Methods for the prevention and/or alleviation of androgen-mediated disorders treatable by administering a chroman-derived anti-androgen compound are provided by the present invention. The invention further provides pharmaceutical and nutraceutical compositions containing chroman-derived anti-androgen compounds useful in the prevention and/or alleviation of androgen-mediated disorders, particularly prostate cancer.

2 Claims, 8 Drawing Sheets

CHROMAN-DERIVED ANTI-ANDROGENS FOR TREATMENT OF ANDROGEN MEDIATED DISORDERS

CROSS-REFERENCE TO RELATED APPLICATIONS

This application is a continuation of U.S. application Ser. No. 13/966,775 filed on Aug. 14, 2013, which is a continuation of U.S. application Ser. No. 13/542,432 filed on Jul. 5, 2012 and issued as U.S. Pat. No. 8,536,219 on Sep. 17, 2013, which is a continuation of U.S. application Ser. No. 12/581, 501 filed on Oct. 19, 2009, which is a continuation of U.S. application Ser. No. 10/789,835 filed on Feb. 27, 2004 and issued as U.S. Pat. No. 7,709,525 on May 4, 2010, which claims the benefit of U.S. provisional Patent Application No. 60/450,510 filed Feb. 27, 2003. Each of these applications is incorporated by reference herein in its entirety.

STATEMENT REGARDING FEDERALLY SPONSORED RESEARCH

This invention was made with government support under DAMD17-98-1-8505 awarded by the ARMY/MRMC. The government has certain rights in the invention.

FIELD OF THE INVENTION

This invention relates generally to chemical antagonists of the androgen receptor. In particular, this invention is directed to chroman-derived anti-androgens and methods of their use for preventing and/or alleviating androgen-mediated disorders such as prostate cancer.

BACKGROUND OF THE INVENTION

As a group, the male sex hormones are termed androgens. Among the androgens, testosterone plays a central role in developing and maintaining secondary male sexual characteristics, including: (1) enlargement of the male sex organs, prostate gland, seminal vesicles and bulbourethral glands; (2) increased growth of body hair, particularly on the face and chest, but sometimes accompanied by decreased growth of hair on the scalp; (3) enlargement of the larynx and thickening of the vocal cords; (4) thickening of the skin; (5) increased muscular growth; and (6) thickening and strengthening of the bones.

Testosterone is normally produced and secreted by interstitial cells of the testes under the influence of luteinizing hormone (LH). LH is a gonadotropin secreted from the anterior lobe of the pituitary gland in response to yet another factor secreted from the hypothalamus, termed luteinizing hormone-release factor (LH-RF). The degree to which male secondary characteristics develop is directly related to the amount of testosterone secreted by the interstitial cells of the testes. This overall amount of testosterone is regulated by a negative feedback system involving the hypothalamus. As the concentration of testosterone in the blood increases, the hypothalamus senses the testosterone via androgen receptors and becomes inhibited, and its stimulation of the anterior pituitary gland by LH-RF is consequently decreased. As the pituitary's secretion of LH is reduced the amount of testosterone released by the interstitial cells of the testes is reduced also. However, as the blood level of testosterone drops, the hypothalamus becomes less inhibited, and it once again stimulates the pituitary gland to release LH. The increasing secretion of LH causes the interstitial cells to release more testosterone, and its blood level rises.

As can be appreciated from the variety of secondary male sexual characteristics, the body possesses a plethora of sex hormone responsive tissues and organs. Unfortunately, many cancers types exhibit susceptibility to sex hormone control mechanisms that regulate growth of the normal organ or tissue from which the neoplasm arose. On the positive side, cancers originating in endocrine organs and the immune system are especially susceptible to medical therapies based on sex hormones, sex hormone antagonists, and/or deprivation. In fact, the sex hormones and their antagonists represent useful agents for the treatment of common cancers arising from the breast, prostate gland, and uterus.

In this regard, the role of traditional surgery in endocrine ablation has diminished as chemical agents have been identified which can replace surgical procedures. For example, surgical castration, also termed orchiectomy, useful in slowing or preventing the progression of androgen-mediated prostate cancer may be "chemically" achieved by administering an anti-androgen in combination with a known LH-RF agonist. The antiandrogen/LH-RF agonist combination effectively lowers the level of testosterone which, if left unchecked, increases the growth rate of testosterone-dependent prostatic neoplasias. Representative LH-RF agonists include leuprolide or goserelin, described in U.S. Pat. Nos. 4,897,256 and 5,510,460, respectively. Useful anti-androgens include flutamide, bicalutamide, or nilutamide. Flutamide is a nonsteroidal antagonist of the androgen receptor sold under the tradename Eulexin, as described in U.S. Pat. Nos. 3,995,060 and 4,474,813. Bicalutamide is a nonsteroidal antagonist of the androgen receptor sold under the tradename Casodex, as described in U.S. Pat. No. 4,636,505. Nilutamide is also a nonsteroidal antagonist of the androgen receptor and is sold under the tradename Nilandron, as described in U.S. Pat. No. 5,023,088.

Unfortunately, the hormonal therapies for prostatic cancer, while offering many patients a noninvasive option to drastic surgical procedures, are commonly accompanied by many complications or side effects. LH-RF agonists including leuprolide and goserelin act to lower testosterone to post-castration levels but these agonists also result in impotence and hot flashes. As well, anti-androgens targeting the androgen receptor, including flutamide and bicalutamide, often cause diarrhea, breast enlargement (a.k.a., gynecomastia), loss of libido, and nausea (Soloway et al., Urology 47 (Supp 1A):33-37, 1996). There have also been case reports of toxic liver effects (Wysowski et al., Annals of Internal Medicine 118(11): 860-864, 1993).

In part, the side effects observed in current chemical therapies are due to the undesirable characteristic of current anti-androgen compounds to cross the blood brain barrier and affect androgen receptors of the central nervous system, apart from peripheral tissues. While androgen receptors have been well studied in the hypothalamus and peripheral tissues, little is known about the actual molecular mechanisms that result in complications including, but not limited to, loss of libido and nausea. Thus, the penetration of the blood brain barrier by current agents is undesirable and improved agents targeting primarily peripheral tissues are extremely desirable.

Another undesirable effect of some of the current anti-androgenic agents is their undesirable ability to exert partial agonist activity in some prostate cancer cells. For example, the anti-androgen flutamide has been shown to stimulate, instead of inhibit, the growth of LNCaP human prostate carcinoma cells in the laboratory setting (The Prostate 14: 103-115 (1989)). This could potentially stimulate, instead of inhibit, the growth of prostate cancers in a subset of patients. Therefore, the most favorable anti-androgens should exhibit pure antagonist activity in regard to the androgen receptor, no matter their biological context (i.e., never act as androgen receptor agonists).

While anti-androgen compounds find use in cancer therapies, these compounds have also found utility in non-cancer-related therapies. For example, androgendependent hirsutism, manifest as excess hair in women, is currently treated with the anti-androgen flutamide. Unfortunately, many of the same side effects described above are experienced by women treated with flutamide due to the general nature of flutamide's antagonist activity.

As can be readily appreciated, the quality of life afforded by current therapies, in particular therapies utilizing anti-androgens, is far less than desirable. Therefore, there exists a need for anti-androgens that offer patients reduced complications while providing effective regimens of therapy. Anti-androgens exhibiting peripheral tissue-specific targeting would be extremely valuable in improving the quality of therapy available to those in need thereof.

SUMMARY OF THE INVENTION

The present invention is based on the inventor's pioneering discovery that the chromanol-derived moiety of vitamin E possesses potent anti-androgenic activity in androgen-dependent cells. In particular, the compound 2,2,5,7,8-pentamethyl-6-chromanol (PMCol) was identified by the inventors as demonstrating pure antagonist activity toward the androgen receptor in prostate carcinoma cell lines. The anti-androgen activity of chromanol-derived compounds was heretofore unknown. The various embodiments of the invention described and claimed herein thusly provide advantageous methods and compositions based on the inventors' unexpected findings.

In one embodiment, the invention is directed to a method for inhibiting the growth of androgen-dependent tumor cells. The method includes the step of administering to the tumor cells an effective amount of an anti-androgen compound according to Formula I:

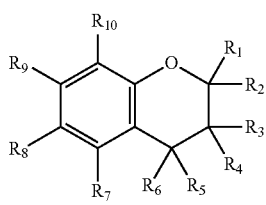

I wherein $R_1$, $R_2$, $R_3$, $R_4$, $R_5$, $R_6$, $R_7$, $R_9$ and $R_{10}$ are independently a substituted or un-substituted $C_1$-$C_3$ alkyl group or H; and $R_8$ is an OH. The anti-androgen compound is water soluble and, in a most preferred embodiment, the anti-androgen compound has the structure of Formula II:

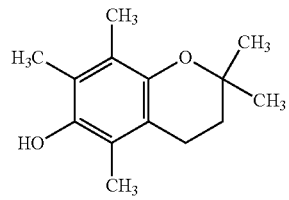

II

In another embodiment, the invention is a method of delaying the progression of prostate cancer in a patient suffering from prostate cancer. The method includes the step of administering to the patient an effective amount of anti-androgen compound according to Formula I. The anti-androgen compound is water soluble and, in a most preferred embodiment, the anti-androgen compound has the structure of Formula II.

In another embodiment, the present invention is a method of preventing the occurrence or recurrence of prostate cancer in a patient at risk thereof. The method includes the step of administering to the patient an effective amount of anti-androgen compound according to Formula I. The anti-androgen compound is water soluble and, in a most preferred embodiment, the anti-androgen compound has the structure of Formula II.

In one embodiment of the invention, a method for the treatment of an androgen-mediated disorder remediable by contacting an androgen receptor with an anti-androgen compound is provided. The method includes the step of administering to a patient an effective amount of an anti-androgen compound having Formula I or its pharmaceutically acceptable salt. In preferred embodiments, the anti-androgen compound reversibly binds to and acts as antagonist of the androgen receptor. The anti-androgen compound is water soluble and, in a most preferred embodiment, the anti-androgen compound has the structure of Formula II.

According to the invention, the androgen-mediated disorder remediable by contacting an androgen receptor with an anti-androgen compound according to Formula I may be, but is not limited to, hirsutism, acne, seborrhea, Alzheimer's disease, androgenic. alopecia, hyperpilosity, benign prostatic hypertrophy, adenomas or neoplasias of the prostate, treatment of benign or malignant tumor cells containing the androgen receptor, modulation of VEGF expression for use as antiangiogenic agents, osteoporosis, suppressing spermatogenesis, libido, cachexia, endometriosis, polycystic ovary syndrome, anorexia, androgen-related diseases and conditions, and male and female sexual dysfunction or infertility. A preferred use of an anti-androgen compound described herein is in the treatment or prevention of prostate cancer.

The present invention is also directed to pharmaceutical and nutraceutical compositions comprising an anti-androgen compound having Formula I in combination with an acceptable carrier.

Other objects, features and advantages of the present invention will become apparent after review of the specification, claims and drawings.

DETAILED DESCRIPTION OF THE INVENTION

I. In General

Figure 1:
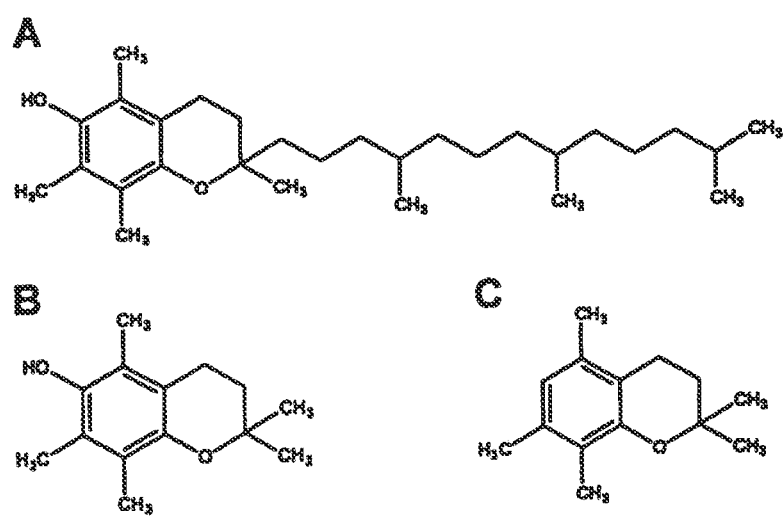
FIG. 1. Structure of vitamin E (i.e., α-tocopherol) and related compounds. A, α-tocopherol. B, 2,2,5,7,8-pentamethyl-6-chromanol (PMCol). C, 2,2,5,7,8-pentamethylchroman (PMC).

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Abbreviations used herein include: AR, androgen receptor; αCEHC, α-carboxyethylhydroxychroman; CSS, charcoal-stripped serum; DMEM, Dulbecco's modified Eagle's medium; FBS, fetal bovine serum; MMTV/LTR, Mouse mammary tumor virus long terminal repeat; PBS, phosphate-buffered saline; PMC, 2,2,5,7,8-pentamethylchroman; PMCol, 2,2,5,7,8-pentamethyl-6-chromanol; PSA, prostate specific antigen; R1881, methyltrienolone.

The Invention

The present invention provides methods of utilizing newly identified anti-androgen compounds. These compounds define a new subclass of compounds useful for preventing or treating a wide variety of androgen-mediated disorders. Compounds useful in the present invention, in particular 2,2,5,7,8-pentamethyl-6-chromanol (PMCol), are derived from the anti-oxidant moiety of vitamin E and have unexpected anti-androgen activity as non-steroidal ligands of the androgen receptor. Because of the chemical structure of PMCol and compounds structurally similar thereto, compounds useful in the present invention exhibit significant solubility in water. Such compounds are particularly desirable as improved anti-androgens as they will not readily cross the blood-brain barrier in amounts significant enough to evoke changes in physiological parameters affected by the androgen receptors of brain tissues residing behind the blood-brain barrier.

Accordingly, the present methods provide therapeutic effects by antagonizing androgen receptors in substantially only peripheral tissues and organs, in contrast to prior androgen receptor antagonists. In general, compounds useful in the present invention will possess a water solubility greater than vitamin E; vitamin E is practically insoluble in water but freely soluble in acetone, ether or equivalent fat solvents. Furthermore, the anti-androgen compounds used according to the invention are pure antagonists and do not exhibit even partial agonist activity, as assayed in, for example, LNCaP human prostate carcinoma cells.

In one particular embodiment, the invention is directed to a method for inhibiting the growth of androgen-dependent tumor cells. This method includes the step of administering to the tumor cells an effective amount of an anti-androgen compound represented by the structure of Formula I:

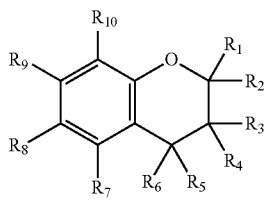

wherein $R_1$, $R_2$, $R_3$, $R_4$, $R_5$, $R_6$, $R_7$, $R_9$ and $R_{10}$ are independently a substituted or un-substituted $C_1$-$C_3$ alkyl group or H; and $R_8$ is an OH. In a preferred embodiment, the above-described method utilizes an anti-androgen compound having Formula II:

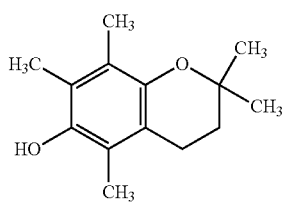

In Formula I, the substituent R is defined as an alkyl group, H or OH, unless otherwise indicated. An "alkyl" group refers to a saturated aliphatic hydrocarbon. The alkyl group has 1-3 carbons, and may be un-substituted or substituted by one or more groups selected from halogen, hydroxy, alkoxy carbonyl, amido, alkylamido, dialkylamido, nitro, amino, alkylamino, dialkylamino, carboxyl, thio and thioalkyl. A "hydroxy" group refers to an OH group. An "alkoxy" group refers to an —O-alkyl group wherein alkyl is as defined above. A "thio" group refers to an —SH group. A "thioalkyl" group refers to an —SR group wherein R is alkyl as defined above. An "amino" group refers to an —NH₂ group. An "alkylamino" group refers to an —NHR group wherein R is alkyl is as defined above. A "dialkylamino" group refers to an —NRR' group wherein R and R' are all as defined above. An "amido" group refers to an —CONH₂. An "alkylamido" group refers to an —CONHR group wherein R is alkyl is as defined above. A "dialkylamido" group refers to an —CONRR' group wherein R and R' are alkyl as defined above. A "nitro" group refers to an NO₂ group. A "carboxyl" group refers to a COOH group.

As contemplated herein, the present invention relates to methods of utilizing an anti-androgen compound and/or its analog, derivative, isomer, metabolite, pharmaceutically acceptable salt, hydrate, N-oxide, or combinations thereof in the treatment or prevention of an androgen-mediated disorder (e.g., prostate cancer). In one embodiment, the invention relates to the use of an analog of the anti-androgen compound. In another embodiment, the invention relates to the use of a derivative of the antiandrogen compound. In another embodiment, the invention relates to the use of an isomer of the anti-androgen compound. In another embodiment, the invention relates to the use of a metabolite of the anti-androgen compound. In another embodiment, the invention relates to the use of a pharmaceutically acceptable salt of the anti-androgen compound. In another embodiment, the invention relates to the use of a hydrate of the anti-androgen compound. In another embodiment, the invention relates to the use of an N-oxide of the anti-androgen compound.

The anti-androgen compounds useful in the present invention are chromanderived chemicals which are either known or obtainable through purification schemes and/or syntheses known to those of skill in the art. For example, a preferred embodiment utilizes the compound of structure II, PMCol, which is available from commercial sources such as Aldrich (Milwaukee, Wis.). Furthermore, compounds structurally related to PMCol, as described herein, may be derived through methodologies disclosed by, for example, Pope et al. in Free Radic. Biol. Med. 33: 807-817 (2002) and Carey et al. in Advanced Organic Chemistry, Parts A and B, Kluwer Academic/Plenum Publishers, 4th Ed. (2001). The synthesis of αCEHC, a metabolite of vitamin E, is described fully by Pope et al. and workers with skill in the art may modify this teaching using techniques known in the field without undue experimentation to arrive at structurally-similar compounds useful in the present invention. Briefly, αCEHC is synthesized in a 2-step process. In the first step, gamma-methyl-gamma-vinylbutyrolactone (MVBL) is synthesized using a Grignard reaction with ethyl levulinate and vinyl magnesium bromide in anhydrous ether. The MVBL intermediate will be purified by high performance liquid chromatography (HPLC). In the second step, (+/−) αCEHC is synthesized by the condensation of trimethylhydroquinone with MVBL in the presence of a Lewis acid and purified using HPLC. αCEHC purity is assessed using nuclear magnetic resonance spectroscopy and liquid-chromatography/mass spectrometry (LC/MS).

By structural comparison, α-CEHC and PMCol are closely related, differing only by the addition of a carboxyethyl group at the 2 position of the chromanol ring. The structure of α-CEHC is set forth below as Formula III:

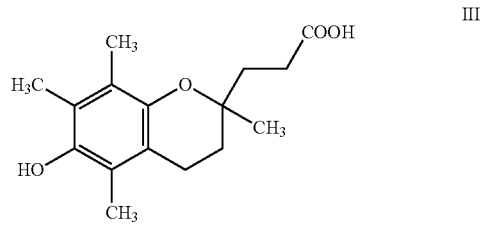 [SMILES: Cc1c(C)c2c(c(C)c1O)CCC(C)(CCC(=O)O)O2]

However, the presence of this carboxyethyl group will alter the chemical properties of PMCol with the carboxyl moiety increasing the charge character of the chromanol compound. The carboxyl moiety thereby increases the compound's water-solubility and thusly promotes improved association of the compound with androgen receptor in the peripheral tissues. The importance of water solubility to chroman-derived compounds useful in the present invention was described above.

As defined herein, the term "isomer" includes, but is not limited to optical isomers and analogs, structural isomers and analogs, conformational isomers and analogs, and the like. In one embodiment, this invention encompasses the use of different optical isomers of an anti-androgen compound of Formula 1. It will be appreciated by those skilled in the art that the anti-androgen compounds useful in the present invention may contain at least one chiral center. Accordingly, the compounds used in the methods of the present invention may exist in, and be isolated in, optically-active or racemic forms. Some compounds may also exhibit polymorphism.

It is to be understood that the present invention encompasses the use of any racemic, optically-active, polymorphic, or stereroisomeric form, or mixtures thereof, which form possesses properties useful in the treatment of androgen-related conditions described and claimed herein. In one embodiment, the anti-androgen compounds are the pure (R)-isomers. In another embodiment, the anti-androgen compounds are the pure (S)-isomers. In another embodiment, the compounds are a mixture of the (R) and the (S) isomers. In another embodiment, the compounds are a racemic mixture comprising an equal amount of the 10 (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes method utilizing derivatives of the anti-androgen compounds. The term "derivatives" includes but is not limited to ether derivatives, acid derivatives, amide derivatives, ester derivatives and the like. In addition, this invention further includes methods utilizing hydrates of the anti-androgen compounds. The term "hydrate" includes but is not limited to hemihydrate, monohydrate, dihydrate, trihydrate and the like.

This invention further includes methods of utilizing metabolites of the antiandrogen compounds. The term "metabolite" means any substance produced from another substance by metabolism or a metabolic process.

As used herein, receptors for extracellular signaling molecules are collectively referred to as "receptors." Many receptors are transmembrane proteins on a cell surface where they contact or bind an extracellular signaling molecule (ie., a ligand). In this manner, the receptors initiate a cascade of intracellular signals that alter the behavior of the cell. In contrast, in some cases, the receptors are located within the cell and the signaling ligand must first enter the cell by passive or active transport to activate the receptor.

Steroids are one example of small molecules that diffuse directly across the plasma membrane of target cells and bind to intracellular receptors. These receptors are structurally related and constitute the intracellular receptor superfamily (or steroid-hormone receptor superfamily). Steroid receptors include progesterone receptors, estrogen receptors, androgen receptors, glucocorticoid receptors, and mineralocorticoid receptors. The present invention is particularly directed to androgen receptors. An androgen receptor is an androgen receptor of any species of, for example, a mammal. In one embodiment, the androgen receptor is an androgen receptor of a human.

The invention is directed to methods utilizing anti-androgen compounds which are antagonist compounds. A receptor antagonist is a substance which contacts or interacts with receptors and inactivates them. Thus, an anti-androgen compound useful in the invention binds and inactivates steroidal receptors.

Assays to measure the anti-androgen activity of chroman-derived compounds, as described herein, are well known to a person skilled in the art. For example, androgen receptor antagonistic activity can be determined by monitoring the ability of a candidate anti-androgen compound to inhibit the growth of androgen-dependent tissue, an example of such an assay being provided in the following Example section.

The compounds useful in the present invention bind either reversibly or irreversibly to an androgen receptor. In one embodiment, the anti-androgen compound binds reversibly to an androgen receptor. In another embodiment, the anti-androgen compound binds reversibly to an androgen receptor of a mammal. In another embodiment, the anti-androgen compound binds reversibly to an androgen receptor of a human. Reversible binding of a compound to a receptor means that a compound can dissociate from the receptor after binding.

In another embodiment, the anti-androgen compound binds irreversibly to an androgen receptor. In one embodiment, the anti-androgen compound binds irreversibly to an androgen receptor of a mammal. In another embodiment, the anti-androgen compound binds irreversibly to an androgen receptor of a human. Thus, in one embodiment, the compounds of the present invention may contain a functional group (e.g. affinity label) that allows alkylation of the androgen receptor (i.e. covalent bond formation). In this case, the compounds are alkylating agents which bind irreversibly to the receptor and, accordingly, cannot be displaced by a steroid, such as the endogenous ligands dihydroxy testosterone (DHT) and testosterone; An "alkylating agent" is defined herein as an agent which alkylates (forms a covalent bond) with a cellular component, such as DNA, RNA or protein. For example, in one embodiment, an alkylating group is an isocyanate moiety, an electrophilic group which forms covalent bonds with nucleophilic groups (N, O, S etc.) in cellular components. In another embodiment, an alkylating group is an isothiocyanate moiety, another electrophilic group which forms covalent bonds with nucleophilic groups (N, O, S etc.) in cellular components. In another embodiment, an alkylating group is a haloalkyl ($CH_2X$ wherein X is halogen), an electrophilic group which forms covalent bonds with nucleophilic groups in cellular components. In another embodiment, an alkylating group is a haloalkyl-amido (NH $COCH_2X$ wherein X is halogen), an electrophilic group which forms covalent bonds with nucleophilic groups in cellular components.

In certain embodiments, the present invention is a method for the treatment of a condition remediable by contacting an androgen receptor with an anti-androgen compound represented by the structure of Formula I. Compounds according to Formula I, either alone or in a pharmaceutical composition, are useful in treating a wide variety of such conditions including, but not limited to, hirsutism, acne, seborrhea, Alzheimer's disease, androgenic alopecia, hyperpilosity, benign prostatic hypertrophy, adenomas or neoplasias of the prostate, treatment of benign or malignant tumor cells containing the androgen receptor, modulation of VEGF expression for use as antiangiogenic agents, osteoporosis, suppressing spermatogenesis, libido, cachexia, endometriosis, polycystic ovary syndrome, anorexia, androgen-related diseases and conditions, male and female sexual dysfunction and infertility.

In another embodiment, the invention is a method of delaying the progression of prostate cancer in a patient suffering from prostate cancer. The method includes the step of administering to the patient an effective amount of anti-androgen compound according to Formula I. The anti-androgen compound is water soluble and, in a most preferred embodiment, the anti-androgen compound has the structure of Formula II.

In yet another embodiment, the present invention is a method of preventing the occurrence or recurrence of prostate cancer in a patient at risk thereof. The method includes the step of administering to the patient an effective amount of anti-androgen compound according to Formula I. The anti-androgen compound is water soluble and, in a most preferred embodiment, the anti-androgen compound has the structure of Formula II.

As defined herein, "contacting" means that the anti-androgen compound used in the present invention is introduced into a sample containing the receptor in a test tube, flask, tissue culture, chip, array, plate, microplate, capillary, or the like, and incubated at a temperature and time sufficient to permit binding of the anti-androgen compound to the receptor. Methods for contacting the samples with the anti-androgen compound or other specific binding components are known to those skilled in the art and may be selected depending on the type of assay protocol to be run. Incubation methods are also standard and are known to those skilled in the art.

In another embodiment, the term "contacting" means that the anti-androgen compound used in the present invention is introduced into a patient receiving treatment, and the compound is allowed to come in contact with the androgen receptor in vivo.

As used herein, the term "treating" includes preventative as well as disorder remittent treatment. As used herein, the terms "reducing," "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-androgen compound according to Formula I. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has an androgen-dependent disorder remediable or treatable by administration of the anti-androgen according to Formula I; or (2) is susceptible to an androgen-dependent disorder that is preventable by administering the anti-androgen according to Formula I.

In one embodiment, the methods of the present invention comprise administering an anti-androgen compound as the sole active ingredient. However, also encompassed within the scope of the present invention are methods for therapy, for treating prostate cancer, for delaying the progression of prostate cancer, for preventing the onset of prostate cancer, and for preventing and/or treating the recurrence of prostate cancer, which comprise administering the anti-androgen compounds in combination with one or more therapeutic agents. These agents include, but are not limited to: LH-RF analogs, other reversible/irreversible anti-androgens, anti-estrogens, anti-cancer drugs, 5-alpha reductase inhibitors, aromatase inhibitors, progestins, or agents acting through other nuclear receptors.

Thus, in one embodiment, the present invention provides methods of administering compositions and pharmaceutical compositions comprising an antiandrogen in combination with an LH-RF analog. In another embodiment, the present invention provides methods of administering compositions and pharmaceutical compositions comprising an anti-androgen compound, in combination with another reversible anti-androgen. In another embodiment, the present invention provides administering compositions and pharmaceutical compositions comprising an antiandrogen compound, in combination with an anti-estrogen. In another embodiment, the present invention provides administering compositions and pharmaceutical compositions comprising an anti-androgen compound, in combination with an anticancer drug. In another embodiment, the present invention provides administering compositions and pharmaceutical compositions comprising an anti-androgen compound, in combination with a 5-alpha reductase inhibitor. In another embodiment, the present invention provides administering compositions and pharmaceutical compositions comprising an anti-androgen compound, in combination with an aromatase inhibitor. In another embodiment, the present invention provides administering compositions and pharmaceutical compositions comprising an anti-androgen compound, in combination with a progestin. In another embodiment, the present invention provides administering compositions and pharmaceutical compositions comprising an anti-androgen compound, in combination with an agent acting through other nuclear receptors.

As used herein, "pharmaceutical composition" means therapeutically effective amounts of the anti-androgen compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of an androgen-mediated disorder (e.g., prostate cancer); and (b) the reversal or stabilization of an androgen-mediated disorder (e.g., prostate cancer). The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, marmitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the prostate, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the antiandrogen compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-androgen compound can be administered to a patient by, for example, subcutaneous implantation of a pellet. In a further embodiment, a pellet provides for controlled release of antiandrogen compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administerable by the invention can be prepared by known dissolving, mixing, granulating, or tablet-forming processes. For oral administration, the anti-androgens or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the anti-androgen compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-androgen compounds or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 10 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

For use in medicine, the salts of the anti-androgen compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In addition, the anti-androgen compounds described herein may be provided in the form of nutraceutical compositions where the anti-androgen compound prevents the onset of or reduces or stabilizes various deleterious androgen-related disorders, e.g., prostate cancer. The term "nutraceutical," or "nutraceutical composition", for the purposes of this specification, refers to a food item, or a part of a food item, that offers medical health benefits, including prevention and/or treatment of disease. A nutraceutical composition according to the present invention may contain only an antiandrogen compound according to the present invention as an active ingredient or, alternatively, may further comprise, in admixture with the aforesaid anti-androgen compound, dietary supplements including vitamins, co-enzymes, minerals. herbs, amino acids and the like which supplement the diet by increasing the total intake of that substance.

Therefore, the present invention provides methods of providing nutraceutical benefits to a patient comprising the step of administering to the patient a nutraceutical composition containing a compound having Formula I or a pharmaceutically acceptable salt thereof. Such compositions generally include a "nutraceutically-acceptable carrier" which, as referred to herein, is any carrier suitable for oral delivery including, but not limited to, the aforementioned pharmaceutically-acceptable carriers. In certain embodiments, nutraceutical compositions according to the invention comprise dietary supplements which, defined on a functional basis, include immune boosting agents, anti-inflammatory agents, anti-oxidant agents, or mixtures thereof.

The immune boosters and/or anti-viral agents are useful for accelerating wound-healing and improved immune function; and they include extracts from the coneflowers, or herbs of the genus *Echinacea*, extracts from herbs of the genus *Sambuca*, and Goldenseal extracts. Herbs of the genus *Astragalus* are also effective immune boosters in either their natural or processed forms. *Astragalus* stimulates development into of stem cells in the marrow and lymph tissue active immune cells. Zinc and its bioactive salts, such as zinc gluconate and zinc acetate, also act as immune boosters in the treatment of the common cold.

Antioxidants include the natural, sulfur-containing amino acid allicin, which acts to increase the level of antioxidant enzymes in the blood. Herbs or herbal extracts, such as garlic, which contain allicin are also effective antioxidants. The catechins, and the extracts of herbs such as green tea containing catechins, are also effective antioxidants. Extracts of the genus *Astragalus* also show antioxidant activity. The bioflavonoids, such as quercetin, hesperidin, rutin, and mixtures thereof, are also effective as antioxidants. The primary beneficial role of the bioflavonoids may be in protecting vitamin C from oxidation in the body. This makes more vitamin C, or ascorbic acid, available for use by the body.

Bioflavonoids such as quercetin are also effective anti-inflammatory agents, and may be used as such in the inventive compositions. Anti-inflammatory herbal supplements and anti-inflammatory compounds derived from plants or herbs may also be used as anti-inflammatory agents in the inventive composition. These include bromolain, a proteolytic enzyme found in pineapple; teas and extracts of stinging nettle; turmeric, extracts of turmeric, or curcumin, a yellow pigment isolated from turmeric.

Another supplement which may be used in the present invention is ginger, derived from herbs of the genus *Zingiber*. This has been found to possess cardiotonic activity due to compounds such as gingerol and the related compound shogaol as well as providing benefits in the treatment of dizziness, and vestibular disorders. Ginger is also effective in the treatment of nausea and other stomach disorders.

Supplements which assist in rebuilding soft tissue structures, particularly in rebuilding cartilage, are useful in compositions for treating the pain of arthritis and other joint disorders. Glucosamine, glucosamine sulfate, chondroitin, and chondroitin sulfate are particularly useful for this purpose. Chondroitin may be derived from a variety of sources, such as Elk Velvet Antler. Marine lipid complexes, omega 3 fatty acid complexes, and fish oil are also known to be useful in treating pain associated with arthritis.

Supplements useful in treating migraine headaches include feverfew and *Gingko biloba*. The main active ingredient in feverfew is the sesquiterpene lactone parthenolide, which inhibits the secretion of prostaglandins which in turn cause pain through vasospastic activity in the blood vessels. Feverfew also exhibits anti-inflammatory properties. Fish oil, owing to its platelet-stabilizing and antivasospastic actions, may also be useful in treating migraine headaches. The herb *Gingko biloba* also assists in treatment of migraines by stabilizing arteries and improving blood circulation.

Although some of the supplements listed above have been described as to their phaqnacological effects, other supplements may also be utilized in the present invention and their effects are well documented in the scientific literature.

The following Examples are offered by way of illustration and not by way of limitation.

III. EXAMPLES

Example 1

Androgen antagonist activity by the antioxidant moiety of vitamin E, 2,2,5,7,8-pentamethyl-6-chromanol, in human prostate carcinoma cells.

Summary

The present inventors have shown that the antioxidant moiety of vitamin E, 2,2,5,7,8-pentamethyl-6-chromanol (PMCol), has anti-androgen activity in prostate carcinoma cells. In the presence of PMCol, the androgen-stimulated biphasic growth curve of LNCaP human prostate carcinoma cells was shifted to the right. The PMCol induced growth shift was similar to that produced by treatment with the pure anti-androgen bicalutamide (i.e., Casodex), indicative of androgen receptor antagonist activity. The concentration of PMCol used was below the concentration required to affect cell growth or viability in the absence of androgen. Using an androgen receptor binding competition assay, PMCol was found to be a potent anti-androgen in both LNCaP and LAPC4 cells, with an $IC_{50}$ of approximately 10 µM against 1 nM R1881 (a stable, synthetic androgen). Prostate-specific antigen release from LNCaP cells produced by androgen exposure with either 0.05 or 1.0 nM R1881 was inhibited 100% and 80%, respectively, by 30 µM PMCol. Also, PMCol inhibited androgen-induced promoter activation in both LNCaP and LAPC4 cells. However, PMCol did not affect androgen receptor protein levels, suggesting that the inhibitory effects of PMCol on androgenic pathways were not due to decreased expression of the androgen receptor. Therefore, growth modulation by the antioxidant moiety of vitamin E in androgen-sensitive prostate carcinoma cells is due, at least in part, to its potent anti-androgenic activity.

Background

The activity of androgens is tissue-specific and mediated through the androgen receptor (AR). The disruption of androgens and AR activity alters the regulation of androgen-sensitive tissues, such as the prostate gland (1). In the prostate, androgens have a central role in normal glandular development and function (2). However, androgens are also necessary for the development of prostate cancer. The role of androgens in prostate cancer development is emphasized by the observation that eunuchs and men that have a mutation in 5a-reductase type II, an enzyme that converts testosterone to the more potent dihydrotestosterone, do not develop prostate cancer (3). The incidence of prostate cancer has continued to rise for the last two decades, currently affecting over 200,000 men in the United States each year (4). Agents that permit the necessary actions of androgen for normal tissue function while reducing the role of androgens in the pathogenesis of androgen-sensitive tissues may serve as a useful means of reducing prostate cancer development. Recently, several agents have been reported to prevent prostate cancer development, such as selenium, lycopene, and vitamin E (5). Due to the biochemical nature of these agents they are believed to act primarily through antioxidant-related pathways. However, the scope of their biological activity has not been extensively investigated.

Vitamin E is a family of naturally occurring dietary factors, which were originally identified as necessary for reproduction (6). α-tocopherol, the most potent form of vitamin E, has two main components; a sixteen-carbon phytyl chain and a chromanol moiety with four methyl group substitutions (7). Biologically, a-tocopherol is thought to act primarily as an antioxidant, reducing oxidative damage to lipids. The chromanol moiety of α-tocopherol is responsible for its antioxidant activity, whereas the phytyl chain increases the lipophilicity of α-tocopherol and contributes to its tissue and subcellular distribution (8). Cell culture studies using a-tocopherol are difficult to perform due to its limited water solubility. However, the antioxidant chromanol moiety of α-tocopherol, PMCol, which does not possess a phytyl chain, is sufficiently water soluble to permit studies in cell culture. α-tocopherol and PMCol are shown in FIG. 1 along with PMC.

Most human prostate carcinoma cell lines are androgen independent. The LNCaP human prostate carcinoma cell line is one of the few cell lines to show demonstrable responses to androgen exposure (9). Interestingly, LNCaP cells produce a biphasic growth response to androgen exposure with growth stimulation occurring at lower doses and growth inhibition occurring in the absence of androgen or in the presence of high androgen levels (9, 10). In addition, a number of androgen-sensitive responses are induced in LNCaP cells. For example, LNCaP cells produce a dose-dependent increase in PSA expression on androgen exposure (11, 12). Also, androgen-sensitive promoters, such as the MMTV promoter, are activated by androgen in LNCaP cells (13). The exquisite sensitivity of LNCaP cells to androgenic stimulation may be due to a mutation in the ligand-binding domain of the androgen receptor (14). To date, the LNCaP prostate cell line has been the most extensively characterized prostate cell line for examining the effects of androgens. More recently, the LAPC-4 cell line has been introduced as another androgen-sensitive human prostate carcinoma cell line that expresses a normal AR (15). However, the response of LAPC-4 cells to androgens is not as pronounced as observed in LNCaP cells. Collectively, the LNCaP and LAPC4 human prostate carcinoma cell lines provide valuable models for investigating androgen-regulated cellular pathways.

Previous studies have focused primarily on the inhibition of prostate cell growth by vitamin E treatment, which may occur through effects on cell cycle regulators (16, 17, 18). Apoptotic responses induced by vitamin E treatment have also been observed in LNCaP cells (19, 20). Interestingly, vitamin E-induced apoptotic responses were enhanced by coadministration of androgen (19). Zhang et al (21) reported that vitamin E succinate reduces the levels of the AR in LNCaP cells, with resultant inhibition of androgen-mediated responses. However, the direct actions of vitamin E and related compounds on androgen receptor activity in prostate cells have not been extensively examined. In the study described below, the androgen receptor antagonist activity and modulation of androgen-sensitive pathways by the vitamin E derivative, PMCol, were investigated by the present inventors in human prostate carcinoma cells.

Materials and Methods

Chemicals. PMCol and PMC were obtained from Aldrich (Milwaukee, Wis.). The chemical structures of $\alpha$-tocopherol, PMCol, and PMC are shown in FIG. 1. Bicalutamide (Casodex) was kindly provided by AstraZeneca Pharmaceuticals (Wilmington, Del.). R1881 and $^3$H-R1881 (87 Ci/mmol) were obtained from Perkin Elmer/NEN Life Science Products (Boston, Mass.). All other chemicals used in these studies were acquired from Sigma Chemical Company (Saint Louis, Mo.).

Cell culture. LNCaP cells were acquired from American Type Culture Collection (Manassas, Va.) and LAPC4 cells were kindly provided by Dr. Robert Reiter (University of California—Los Angeles) and maintained in DMEM containing 5% heat-inactivated fetal calf serum (Sigma) with streptomycin-penicillin antibiotics (designated DMEM/FBS) in a 5% $CO_2$ incubator at 37° C. For experiments evaluating androgenic responses, cells were cultured in phenol red-free DMEM (Gibco/BRL, Carlsbad, Calif.) 0.5 containing 4% charcoal-stripped fetal calf serum and 1% unstripped fetal calf serum (designated DMEM/CSS).

Androgen receptor binding competition assay. An androgen receptor binding competition assay was performed as previously described (22). LNCaP or LAPC4 prostate carcinoma cells were plated in 12-well tissue culture dishes (Costar, Corning, 10 NY) at $3.0\times10^5$ cells per well in phenol-red free DMEM/CSS 3 d prior to analysis. For competitor analysis, DMEM/CSS was removed by aspiration and replaced with 1 mL of phenol-red free DMEM containing 1 nM $^3$H-R1881, 1 µM triamcinolone acetonide, and competitor at the specified concentrations for 2 h at 37° C. in a 5% $CO^2$ incubator. After incubation, competitor solution was aspirated and cells were removed from the plate by trypsinization and placed in 12×75 mm polystyrene tubes. Cells were washed twice with 1 mL phenol red-free DMEM and placed in 8.0 mL of ScintiVerse II Scintillation Cocktail (Fisher Scientific, Pittsburgh, Pa.) for determination of radioactivity (i.e., dpm) using a Beckman LS 6000TA Liquid Scintillation System (Beckman Instruments Inc., Fullerton, Calif.).

Cell growth and viability analyses. Five thousand LNCaP or LAPC4 cells were plated in each well of 96-well plates (Costar) in 100 µl of DMEM/CSS. Two to 3 d after plating, cells were treated by adding 100 µl of DMEM/CSS containing 2× the concentration of the specified treatment to each well. Four d after treatment, the relative cell number was estimated by the determining DNA concentration of each well using a Hoechst-based fluorescence DNA assay, as previously described (23). Growth analysis with DU145 cells was performed similar to those with LNCaP and LAPC4 cells except DU145 cells were initially seeded at 500 cells per well. Cell viability was determined by trypan blue exclusion and quantified by light microscopic analysis using a hemacytometer.

Determination of secreted PSA levels. LNCaP cells were cultured in 96 well plates (Costar) at 5,000 cells per well in DMEM/CSS 1 d before treatment. Forty-eighth after treatment, PSA levels in cell culture media were determined using the Tandem-MP PSA kit (Beckman Coulter, Inc.) according to manufacturer's instructions. PSA levels were normalized to DNA levels as determined using a Hoechst-based fluorescence DNA assay (23).

Androgen-stimulated promoter reporter assay analysis. LNCaP and LAPC4 prostate carcinoma cell lines were cultured in 12-well cell culture plates (Costar) in DMEM/CSS 2 to 3 d before transfection. Androgen-induced transcriptional activation was determined using a reporter construct with an MMTV promoter that regulates the expression of luciferase (24). LNCaP and LAPC4 cells were transfected with the MMTV/luciferase plasmid using the Effectene Transfection Reagent (Qiagen Inc., Valencia, Calif.), according to the manufacturer's instructions. Twenty-four h after transfection, cells were treated with R1881 with or without test reagents at the specified concentrations. Cell extracts were acquired 24 to 48 h after treatment by removing medium, washing 1× with PBS, and obtaining extract with 200 µL of 1× Reporter Lysis Buffer (promega, Madison, Wis.). Luciferase activity was determined as previously described (24).

Immunoblot analysis of AR protein levels. LNCaP cells were plated at a density of $1\times10^6$ cells per 100 mm cell culture plate in 10 ml of DMEM/FBS and maintained in incubators at 37° C. in 5% $CO_2$. After 5 d of treatment with vehicle, 30 µM PMC, 30 µM PMCol, or 1.0 µM bicalutamide, cells were washed in cold 1×PBS and lysed in a buffer containing 1.0% Nonidet P-40, 0.5% sodium deoxycholate, 0.1% sodium dodecyl sulfate, 0.1 mg/ml phenylmethylsulfonyl fluoride, 1 mM sodium orthovanadate, and 10 µg/ml aprotinin in 1×PBS. Total protein (10 µg) from cell extracts were electrophoresed 10 on 7.5% SDS-polyacrylamide gels and transferred to Immobilon-P membranes (Millipore Corp., Bedford, Mass.) using a GENIE wet transfer system (Idea Scientific, Minneapolis, Minn.). Membranes were blocked in Tris-buffered saline containing 5% nonfat dry milk at and then incubated with mouse anti-AR (441) monoclonal antibody (Santa Cruz Biotechnology, Santa Cruz, Calif.) and mouse anti-actin antibody (A5441; Sigma). Membranes were then incubated with a secondary horseradish peroxidase conjugated anti-mouse antibody (Amersham Pharmacia Biotech, Piscataway, N.J.) and analyzed using the Enhanced Chemiluminescence Plus reagent (Amersham Pharmacia Biotech). Autoradiograms were prepared by exposing the blots to BioMax Light X-ray film (Eastman Kodak Co., Rochester, N.Y.) and developed using a CURIX 60 CP 20 Processor (Agfa, Ridgefield Park, N.J.).

Statistical analysis. Significant differences in values between groups were assessed using a two-sided Student's T-test. P values less than 0.05 were used to signify statistical significance.

Results

Figure 2:
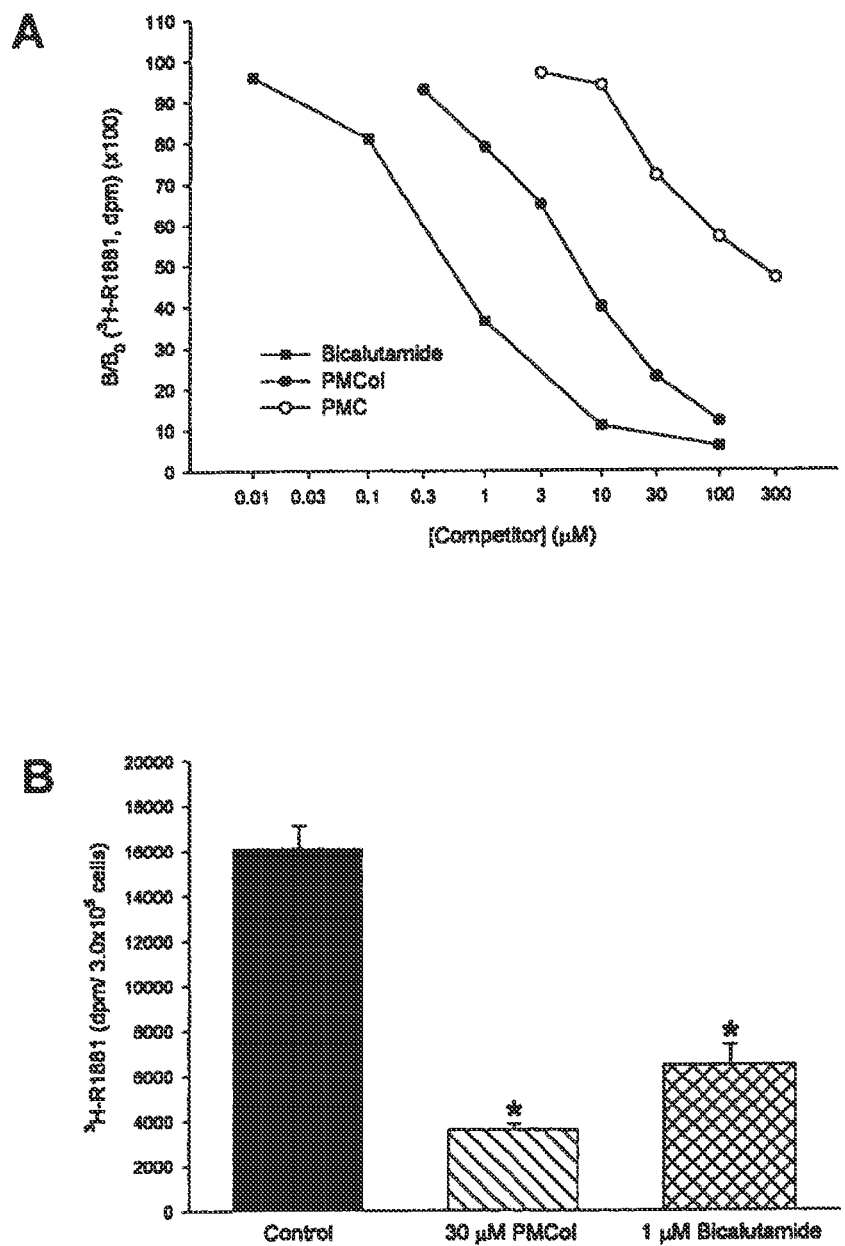
FIG. 2. PMCol competition analysis of R1881 binding in human prostate carcinoma cells. A, A dose-response for the competition of PMCol, PMC, and bicalutamide for androgen receptor binding to $^3$H-R1881 was determined in LNCaP cells. B, Competition for $^3$H-R1881 binding in LAPC4 cells was determined for 30 μM PMCol and 1 μM bicalutamide. (*P<0.05; n=4.)

PMCol Inhibits Androgen Binding in Prostate Cancer Cells. AR competition was determined using 3H-R1881 in the androgen-sensitive LNCaP cell line, which expresses a functional mutant AR (25), and the LAPC4 cell line, which express a normal human AR (15). Increasing concentrations of the AR antagonist bicalutamide were found to progressively inhibit R1881 binding (FIG. 2A), with an estimated $IC_{50}$ of 0.7 µM in 10 LNCaP cells. PMCol was found to be approximately 10-fold less potent at competing for $^3$H-R1881 than bicalutamide in LNCaP cells, with an estimated $IC_{50}$ of 7.2 µM (FIG. 2A). Repeated studies of PMCol competition for $^3$H-R1881 binding gave $IC_{50}$ values ranging from 5 to 15 µM (data not shown). In contrast, PMC, in which the 6-hydroxyl of PMCol is absent, had less anti-androgenic activity than PMCol (FIG. 2A) and significantly reduced cell viability at a concentration of 100 µM within 2 h of treatment (data not shown). Based on the R1881 competition results in LNCaP cells (FIG. 2A), a dose of 30 µM PMC and PMCol was used in most of these studies, allowing an effective comparison of the anti-androgenic activity between PMC and PMCol. In LAPC4 cells, treatment with 30 µM PMCol produced a 75% decrease in $^3$H-R1881 binding and 20 treatment with 1 µM bicalutamide produced a 62% decrease in $^3$H-R1881 binding (FIG. 2B).

Figure 3:
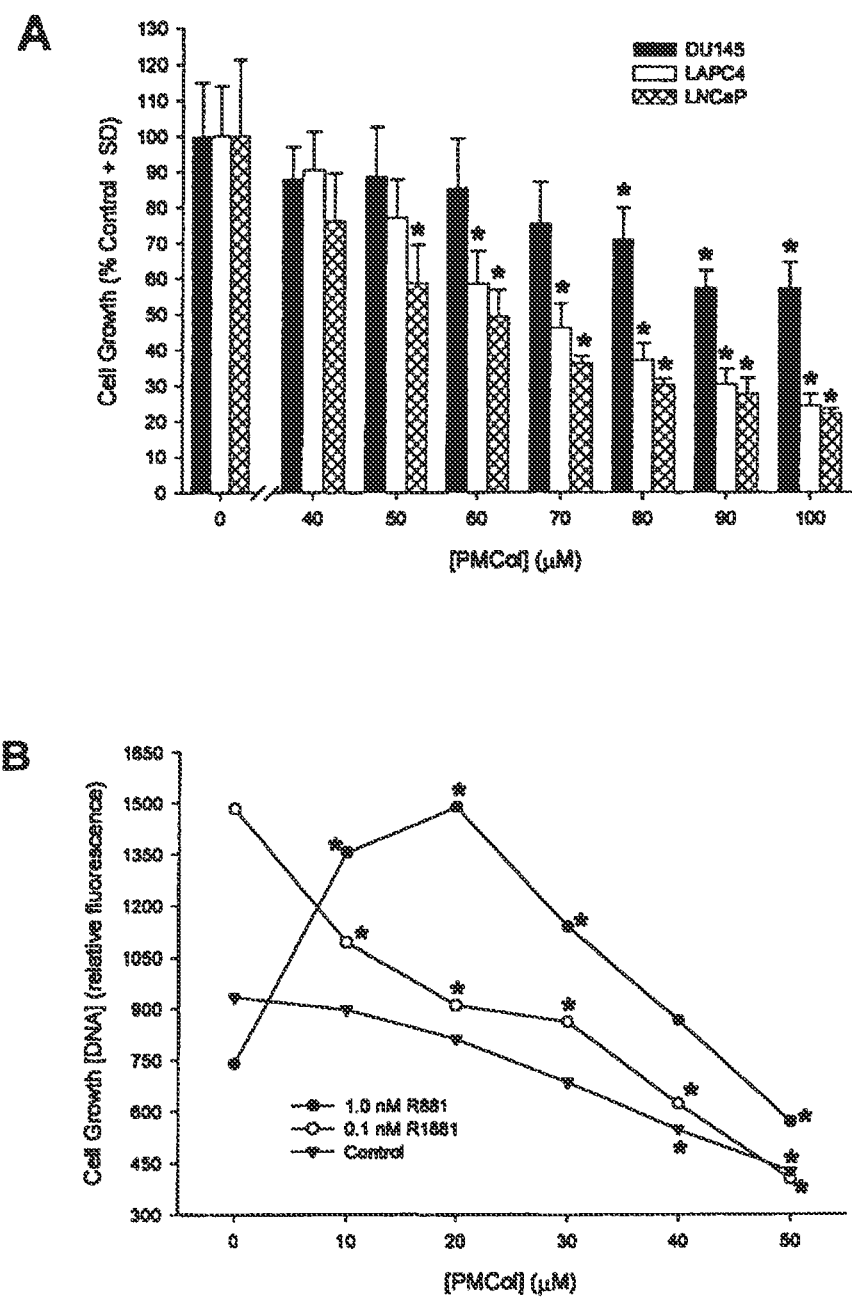
FIG. 3. Growth modulation of human prostate carcinoma cells by PMCol. A, Dose-response of DU145, LAPC4, and LNCaP cells grown in medium containing 5% serum measured 4 d after PMCol treatment. Treatment with 50 μM PMCol significantly reduced LNCaP prostate cell growth, whereas a concentration of 80 μM PMCol was required to significantly decrease growth in the androgen-independent DU145 prostate cell line (*P<0.05). B, The PMCol dose-response of LNCaP cell growth was determined in cells exposed to androgen-deficient conditions (i.e., using medium containing reduced androgen levels) with or without the addition of a growth-stimulatory dose of 0.05 nM R1881 or a growth-inhibitory dose of 1.0 nM R1881. (* significantly different than 0 μM PMCol-treated cells; P<0.05; n=6.)

Modulation of prostate carcinoma cell growth and viability by PMCol. Changes in growth of the androgen-independent DU145 prostate carcinoma cell line and the androgen-sensitive LNCaP and LAPC4 prostate cell lines were assessed at concentrations of PMCol ranging from 10 to 100 µM (FIG. 3A). Concentrations of 50 µM, 60 µM, and 80 µM or more PMCol were required to significantly reduce cell growth in LNCaP, LAPC4, and DU145 cells, respectively (FIG. 3A). LNCaP cells produce a biphasic growth response to androgen exposure (9). Modulation of LNCaP cell growth by PMCol treatment was examined over 4 d. PMCol had no growth modulatory activity in vehicle-control treated LNCaP cells grown in androgen-deficient media (i.e., PMCol did not have AR agonist activity) at concentrations ranging from 10 µM to 30 µM PMCol (FIG. 3B).

Figure 4:
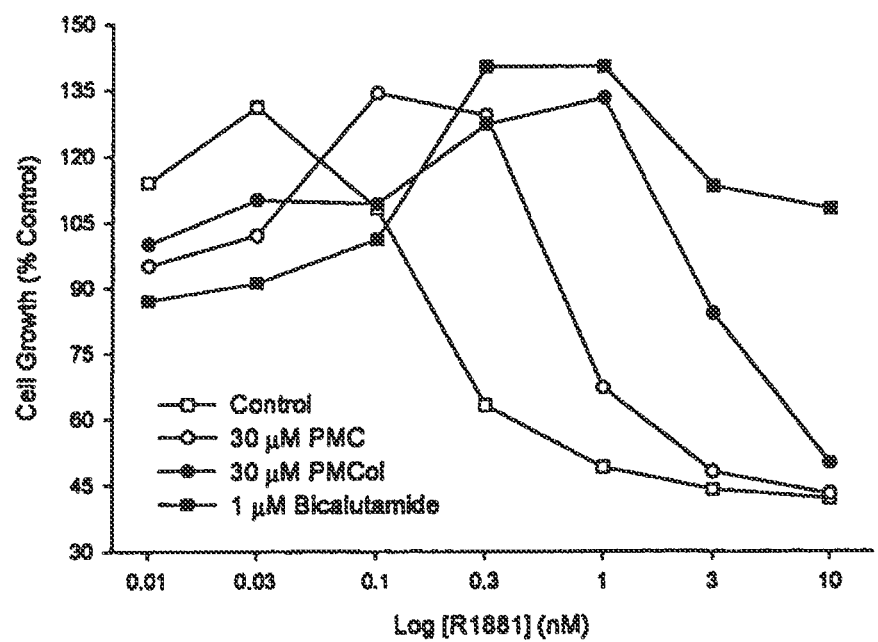
FIG. 4. Shifts in the R1881-stimulated biphasic LNCaP growth response were determined after treatment with 30 μM PMCol, 30 μM PMC, or 1 μM bicalutamide for 4 d. The inhibition of growth response is readily apparent at 0.3 nM R1881 exposure, where LNCaP growth from PMCol, PMC, and bicalutamide treatment was equivalent to the growth response in control cells produced by exposure to only 0.03 nM R1881.

However, LNCaP cell growth was decreased at concentrations equal to or higher than 40 µM PMCol (FIG. 3B) and PMCol concentrations of 100 µM or greater produced significant cell death at 48 and 96 h (Table I). Stimulation of LNCaP growth by exposure to 0.1 nM R1881 was significantly inhibited by treatment with concentrations of 10 µM or more PMCol (FIG. 3B). However, a significant stimulation in LNCaP cell growth was observed in the presence of a normally growth inhibitory concentration of 1.0 nM R1881 with treatment of 10 µM to 30 µM PMCol (FIG. 3B). The R1881-stimulated growth curve of LNCaP cells was shifted to the right in the presence of 30 µM PMCol, similar to that produced by treatment with 1 µM bicalutamide (FIG. 4). A more modest, but significant, shift to the right in the androgen-induced LNCaP growth curve was observed by treatment with 30 µM PMC (FIG. 4).

TABLE 1

Time-and dose-dependent changes in LNCaP cell viability after PMCol treatment
% Cell Viability$^a$ (SD)
[PMCol] (µM)

| Time (h) | 0 | 25 | 50 | 75 | 100 | 250 |
|---|---|---|---|---|---|---|
| 48 | 92.3 | 90.0 | 88.0 | 80.0 | 71.0 | 11.0 |
|  | (4.7) | (2.8) | (3.4) | (12.5) | (8.7)$^b$ | (8.6)$^b$ |
| 96 | 88.0 | 87.0 | 85.0 | 87.0 | 21.0 | 2.0 |
|  | (2.5) | (4.8) | (4.6) | (4.0) | (3.3)$^b$ | (1.8)$^b$ |

$^a$Determined by trypan blue exclusion analysis and quantified using a hemacytometer.
$^b$Significantly different compared to 0 µM PMCol (P < 0.05; n = 4).

Figure 5:
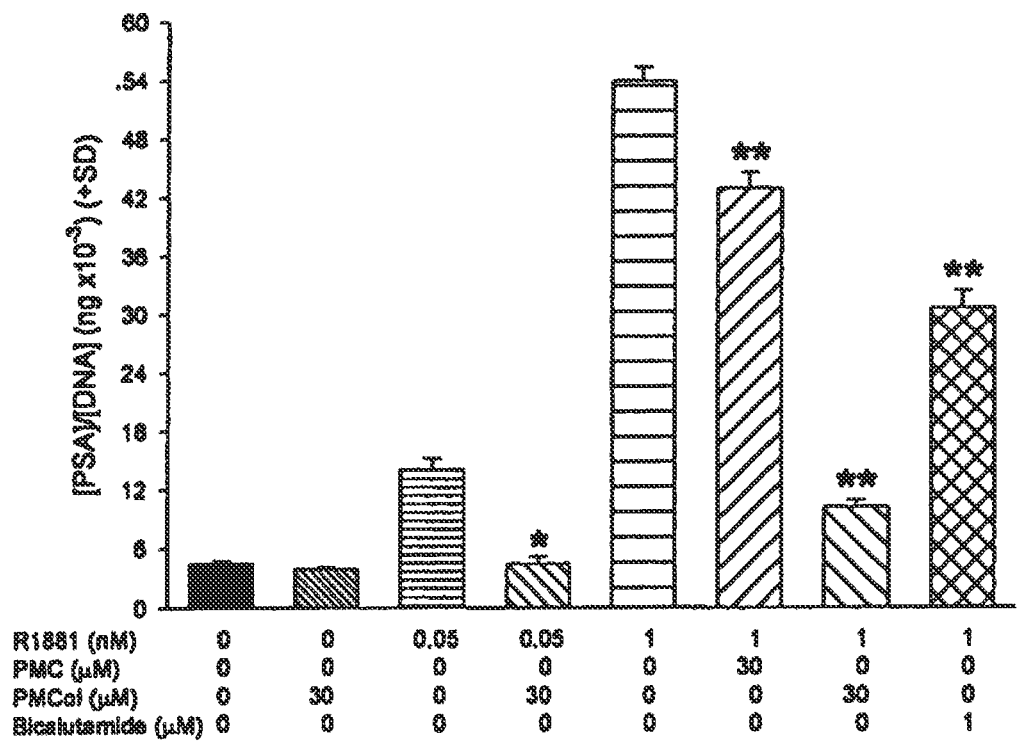
FIG. 5. Analysis of PMCol effects on androgen-induced PSA secretion from LNCaP cells. PSA secretion was determined 48 h after exposure to a growth stimulatory dose of 0.05 nM R1881 or a growth inhibitory dose of 1.0 nM R1881 in the presence of 30 μM PMC, 30 μM PMCol, or 1 μM bicalutamide. (*P<0.05 compared to 0.05 nM R1881 treated cells; **P<0.05 compared to 1.0 nM R1881 treated cells; n=3.)

Inhibition of PSA secretion by PMCol in LNCaP cells. PSA secretion by LNCaP cells is stimulated by androgen exposure in a dose-dependent marmer (12). The R1881-stimulated production of PSA from LNCaP cells was measured after PMCol treatment for 48 h. PSA release from LNCaP cells was not affected by treatment with 30 µM PMCol alone (FIG. 5). However, PSA levels were increased 3.1-fold after exposure to a growth stimulatory dose of 0.05 nM R1881, which was completely inhibited by treatment with 30 µM PMCol (FIG. 5). Exposure of LNCaP cells to 1.0 nM R1881 produced a 12-fold increase in PSA levels by 48 h, which was decreased 20%, 81%, and 43% by treatment with 30 µM PMC, 30 µM PMCol, or 1 µM bicalutamide, respectively (FIG. 5).

Figure 6:
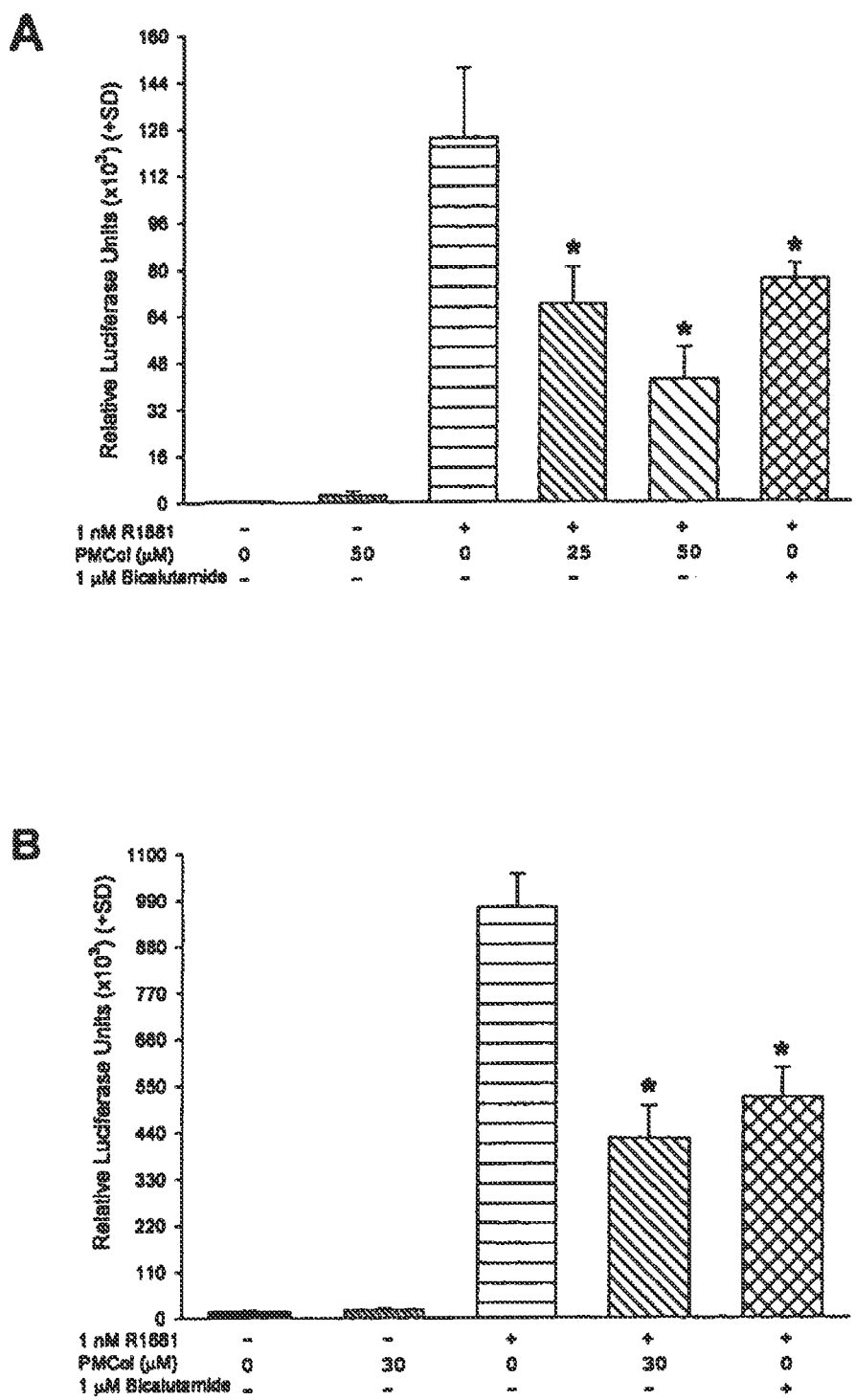
FIG. 6. Androgen-induced MMTV promoter activity in LNCaP (A) and LAPC4 (B) cells after PMCol treatment. A, The effects of 25 μM PMCol, 50 μM PMCol, and 1 μM bicalutamide treatment for 24 h on MMTV promoter activity induced by R1881 was assessed in LNCaP cells. B, LAPC4 cells exposed to 30 μM PMCol effectively inhibited androgen-induced MMTV promoter activity. (*P<0.05; n=4.)

Inhibition of androgen-stimulated transcriptional activation by PMCol. Studies on androgen-regulated transcriptional activation were performed in LNCaP and LAPC4 cells transiently transfected with a reporter vector that uses the androgen-sensitive MMTV/LTR to drive expression of a luciferase reporter gene. In LNCaP cells, PMCol treatment alone had no effect on MMTV promoter activity, whereas luciferase expression was increased 54-fold after exposure to 1.0 nM R1881 for 24 h (FIG. 6A). Luciferase expression induced by exposure to 1.0 nM R1881 in LNCaP cells for 24 h was decreased 50% and 70% by treatment with 25 µM and 50 µM PMCol, respectively (FIG. 6A). Similarly, LAPC4 cells exposed to 1.0 nM R1881 produced a 20-fold increase in MMTV/LTR driven luciferase expression that was decreased 60% by treatment with 30 µM PMCol after 24 h (FIG. 6B). In both LNCaP and LAPC4 cells, treatment with 1 µM bicalutamide decreased 1.0 nM R1881-stimulated luciferase expression approximately 50% (FIGS. 6A and 6B).

Figure 7:
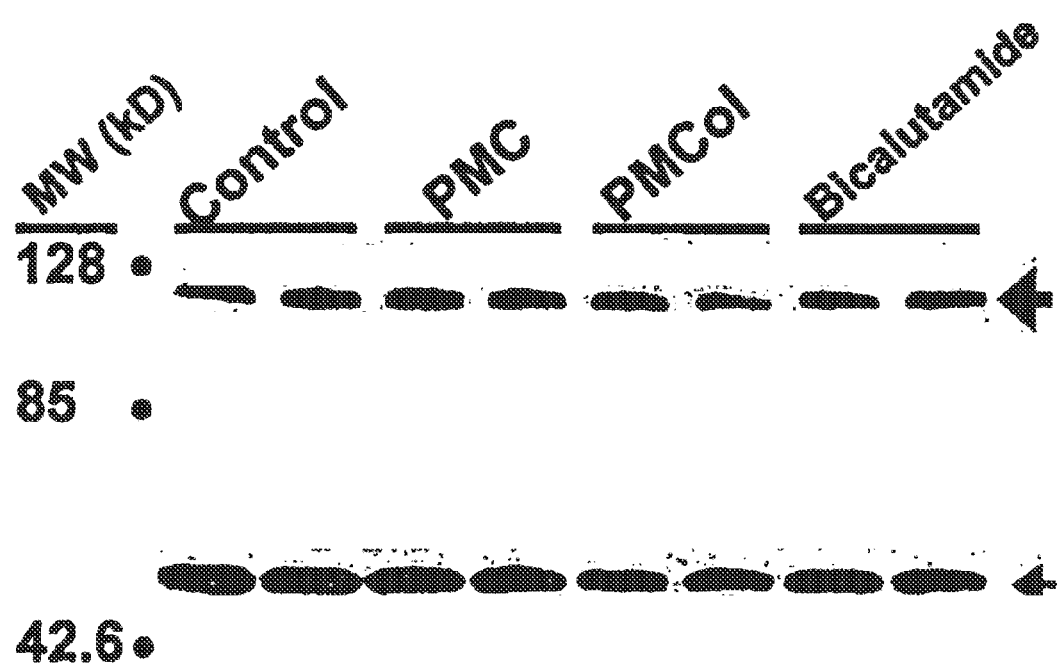
FIG. 7. Immunoblot analysis of AR protein levels. AR protein levels were not significantly altered in LNCaP cells exposed to 30 μM PMC, 30 μM PMCol, or 1 μM bicalutamide for 5 d compared to AR levels in vehicle control exposed cells. LNCaP cells were grown in medium containing 5% serum to provide endogenous serum androgens, thus allowing anti-androgenic modulation of AR protein levels. Large arrow points to AR protein bands and the small arrow points to β-actin protein bands.

Androgen receptor protein levels in PMCol exposed LNCaP cells. Previous studies in LNCaP cells have reported that AR levels are decreased after treatment with vitamin E analogs, which may account for the reduced sensitivity of these cells to androgen exposure (21). However; in the current study, LNCaP cells treated with 30 µM PMC, 30 µM PMCol, or 1 µM bicalutamide for 5 d did not result in altered AR protein levels (FIG. 7).

Discussion

In the current study, the inventors examined the effects of an agent traditionally considered as an antioxidant on prostate carcinoma cells. Epidemiological studies provide intriguing evidence that antioxidant dietary factors such as β-lycopene and vitamin E may help prevent prostate cancer development (5). Although these agents have been classified as antioxidants, the mechanism by which they may contribute to prostate cancer prevention has not been firmly established. Androgens are known to have an essential role in prostate cancer development (3). Modulation of androgen activity may provide a means of prostate cancer prevention (26). Here, the inventors have determined the antioxidant-moiety of vitamin E, PMCol, to be a potent anti-androgen in androgen sensitive human prostate carcinoma cells.

The LNCaP human prostate carcinoma cell line is one of the few prostate cell lines that show demonstrable physiologic changes resulting from androgen exposure, such as growth modulation (9). Therefore, the LNCaP cell line has proven valuable in identifying agents that alter androgen-stimulated cell growth. In the current study, PMCol shifted the androgen-mediated growth curve in LNCaP cells such that higher androgen concentrations were necessary to produce the biphasic growth response typically observed in LNCaP cells. The LNCaP growth shift with PMCol treatment was sufficient to produce growth stimulation in the presence of 1.0 nM R1881, a concentration of R1881 that typically inhibits LNCaP proliferation (10). The shift in LNCaP growth pattern observed with PMCol treatment was similar to that observed in LNCaP cells after treatment with the pure anti-androgen bicalutamide. Also, the $IC_{50}$ of PMCol observed in an androgen competition analysis for R1881 binding in LNCaP cells is in agreement with the dose-response shift in androgen-mediated growth of LNCaP cells after PMCol treatment. Together, these results suggest that the shift observed in the androgen-mediated growth of LNCaP cells was due to the anti-androgenic activity of PMCol.

Although LNCaP cells have proven to be useful in evaluating androgen responsive pathways, the use of LNCaP cells to assess anti-androgenic activity can be inaccurate since LNCaP cells harbor a mutant AR (25). The AR receptor in LNCaP cells, which although functional, has been reported to have altered ligand binding affinity (14) and is stimulated by some agents that are antagonists for the wild-type AR (22). Therefore, in this study, competition for AR binding by PMCol was also assessed in the LAPC4 human prostate carcinoma cell line, which expresses a wild-type AR (15). PMCol competition for R1881 binding was found to be similar for LNCaP and LAPC4 cells. In addition, the pure anti-androgen bicalutamide was found to have equivalent AR competition activity in LNCaP and LAPC4 cells. Therefore, the pure anti-androgen bicalutamide and PMCol were found to possess comparable AR antagonist activity in LNCaP cells, expressing a functional mutant AR, and LAPC4 cells, which express a normal AR.

The AR functions primarily as a transcription factor that is activated by androgen binding (1). In these studies, the androgen-responsive MMTV promoter was used to assess modulation of androgen-stimulated transcriptional activity. Upon androgen exposure (i.e., R1881), MMTV promoter activity was stimulated in both LNCaP and LAPC4 cells. Also, in both cell lines, R1881-stimulation of MMTV activity was significantly inhibited by PMCol treatment. PMCol treatment alone did not stimulate MMTV promoter activity (i.e., PMCol was not found to have AR agonist or partial agonist activity). The effects of androgen exposure on transcriptional activation were further observed by the inhibition of androgen-stimulated PSA release after treatment with PMCol in LNCaP cells. Previously, vitamin E succinate was reported to inhibit the effects of androgen on LNCaP cells through down-regulation of androgen receptor levels (21). Other agents, such as curcumin, have been shown to decrease AR expression in LNCaP cells (27). In the current study, LNCaP cells treated with 30 µM PMCol for five days did not affect AR protein levels. Then, PMCol was found to be a potent inhibitor of transcriptional activation of androgen-responsive promoters, likely through directly blocking AR activation by androgen.

In the current study, PMC, which lacks the phenolic hydroxyl group present on PMCol, was less potent than PMCol at inhibiting androgenic responses. Therefore, the phenolic hydroxyl group of the chromanol ring contributes significantly to the antiandrogenic activity of PMCol. Other forms of vitamin E, such as β-, γ-, and δ-tocopherol differ from α-tocopherol by the number and location of methyl group substitutions on the chromanol ring (7). The inventors can propose that the antioxidant moieties of other forms of vitamin E also possess anti-androgenic activity with potencies that vary dependent on the specific methyl group substitutions present on the chromanol ring.

A variety of dietary agents have been identified that have anti-androgenic activity in prostate carcinoma cells. However, the mechanism of anti-androgenic activity observed by dietary anti-androgens may vary. For example, curcumin, a component of turmeric, was reported to down-regulate androgen receptor protein levels in LNCaP cells, which effectively attenuates androgenic responses (27). In contrast, indole-3-carbinol, a component of cruciferous vegetables, when converted to diindolylmethane was reported to act as a potent inhibitor of androgen binding in LNCaP cells, but does not affect AR protein levels (28). Zhang et al. (21), have reported that vitamin E succinate is inhibitory to androgenic responses in LNCaP cells through down-regulation of AR protein levels, similar to the action of curcumin. By contrast, in the current study, the inventors found that the antioxidant moiety of vitamin E, PMCol, effectively blocks androgen binding to the AR without affecting AR protein levels, similar to effects observed with indole-3-carbinol derivatives (28). Therefore, dietary anti-androgens may serve as an effective means of modulating androgenic pathways through a variety of mechanisms affecting AR activity.

PMCol has largely been investigated for its antioxidant activity associated with being the antioxidant moiety of vitamin E. For example, the antioxidant potency of PMCol was shown to be similar to α-tocopherol in vitro (29). In general, α-tocopherol plasma levels range between 5 and 30 µM (30), well within the range of anti-androgenic activity observed by PMCol in the current study. Due to the high lipophilicity of vitamin E, it is difficult to assess its anti-androgenic activity by cell culture analysis. However, due to the presence of the highly lipophilic phytyl chain, the subcellular distribution of vitamin E would limit its direct interaction with the AR, which resides in more aqueous subcellular compartments such as the cytoplasm and nucleus Vitamin E can be metabolized to derivatives with greater water solubility, such as αCEHC (7, 31), which are structurally similar to PMCol, and may have greater water solubility and a distinct cellular bioavailability compared to vitamin E. Thus, metabolites of vitamin E may contact the AR in vivo and have anti-androgenic activity, analogous to that produced by PMCol in human prostate carcinoma cells.

In summary, the antioxidant moiety of α-tocopherol, PMCol, was found by the present inventors to inhibit androgen activity, likely through competing for androgen binding to the AR, with resultant inhibition of androgen-sensitive biological pathways. PMCol was not found to possess androgen agonist or partial agonist activity and hence functions as a pure antagonist of androgen activity in the LNCaP and LAPC4 prostate carcinoma cell lines. Based on the results of the current study, PMCol will serve as a useful agent for modulating androgen activity in vivo. Importantly, the anti-androgenic activity of PMCol poses the possibility that the prostate cancer preventive activity of vitamin E may, in part, be due to anti-androgenic effects of vitamin E or metabolites of vitamin E in the prostate. Currently, over 30,000 men die from prostate cancer each year in the United States (4). The prevention of prostate cancer through the action of PMCol and derivatives thereof, offers an effective means of reducing the devastation produced by this disease.

Example 2

Figure 8:
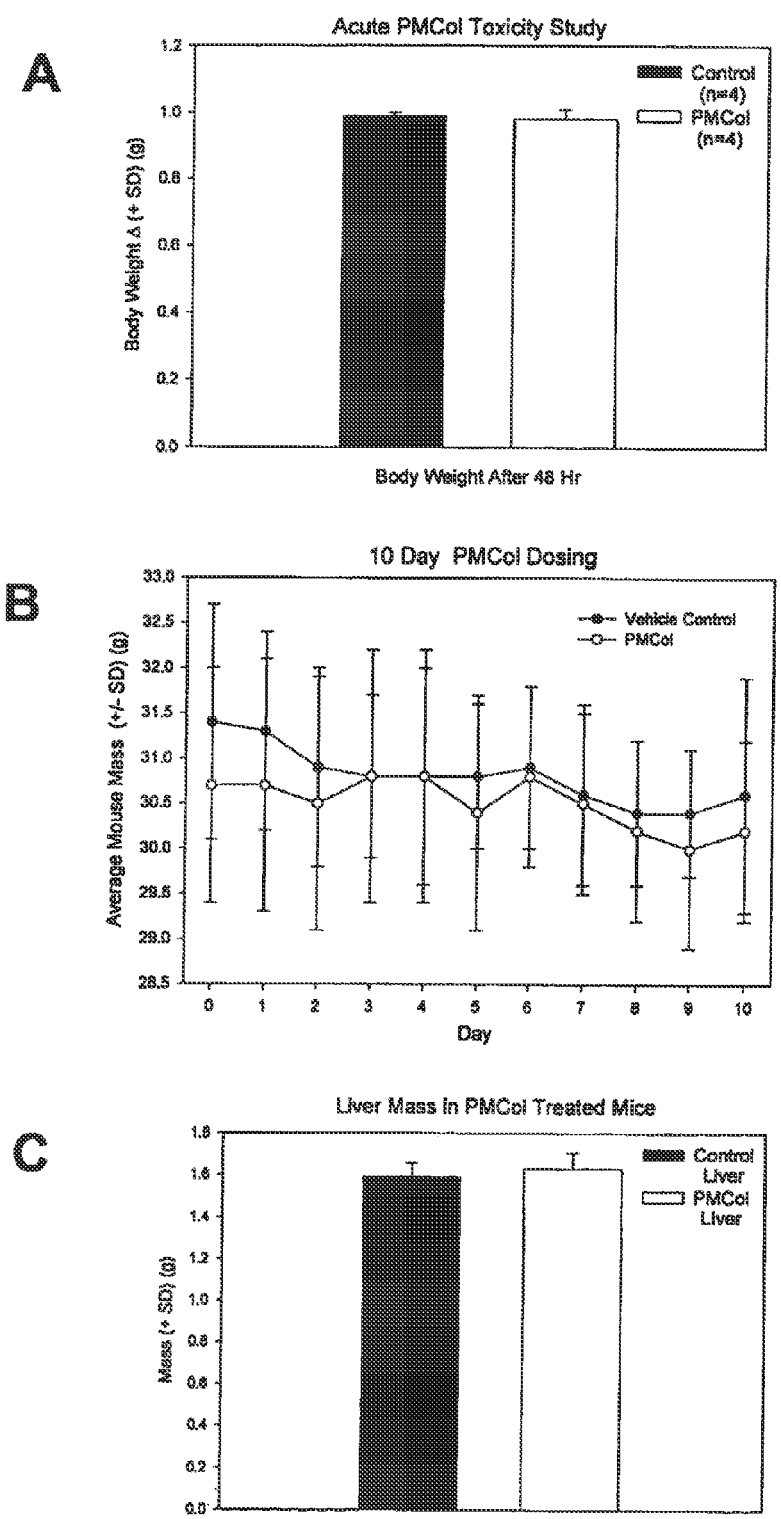
FIG. 8. Acute oral toxicity data for mice. A.) This graph shows that no significant change in animal body mass occurred after administration of a single, high-dose of PMCol compared to vehicle control at 48 hours after PMCol administration. B.) No significant difference in body mass change was observed in comparing mice treated daily with PMCol or vehicle over 10 days. C.) No gross changes in organs were observed for either PMCol-treated or control mice as exemplified by data on liver mass which was not significantly changed in mice receiving PMCol daily for 10 days.

Acute Oral Toxicity in Mice. The oral toxicity of PMCol was determined in 6 month-old male FVB mice. A single high oral dose of 1000 mg/kg PMCol in sesame oil was administered to 4 mice by gavage. Four control mice received only sesame oil by gavage (vehicle control). No significant change in animal behavior or body mass (FIG. 8A) occurred after administration of PMCol or vehicle control for up to 1 week after PMCol administration. In a second study, four 6 month-old male FVB mice received 200 mg/kg PMCol daily in sesame oil by gavage for 10 days. Three mice receiving only sesame oil (vehicle control) were used as controls. Body weights were determined daily and all mice were autopsied to examine gross organ changes on day 11. No significant difference in body mass change was observed in comparing PMCol-treated and vehicle control mice over 10 days (FIG. 8B). No gross changes in organs were observed for either PMCol-treated or control mice. For example, liver mass was not significantly changed in mice receiving PMCol for 10 days (FIG. 8C). Therefore, the LD50 of PMCol in mice is greater than the highest dose tested (i.e., 1000 mg/kg body weight) and PMCol is well tolerated in mice at high doses for up to 10 days.

Example 3

Determining in vivo efficacy of a chroman-derived antiandrogen using the LNCaP xenograft model and the TRAMP prostate carcinogenesis model. A nude mouse/LNCaP xenograft model, similar to the DU145 xenograft method previously described (Church et al., Cancer Chemother. Pharmacol. 43:198-204 (1999)), may be used to examine the in vivo actions of PMCol on human prostate carcinoma cell growth. Male Hsd: athymic nude-nu (nu/nu, BALB/c origin) mice at 4 weeks of age will 10 be acquired from Harlan Sprague Dawley (Madison, Wis.). At 6 weeks of age, each mouse will be subcutaneously xenografted with 106 LNCaP cells in 0.1 mL of medium+0.1 mL of Matrigel (BD Biosciences) in flanking ventral fat pads. One week after LNCaP xenografting, mice will be divided into 5 treatment groups of 10 mice each. Mice in group 1 will receive a vehicle control of 0.25 mL of corn oil by gavage, group 2 will receive 25 mg/kg of flutamide (Sigma Chemical Co., St. Louis, Mo.) as an antiandrogen treatment control, group 3 will receive 25 mg/kg of PMCol in 0.25 mL corn oil, and group 4 will receive 100 mg/kg of PMCol in 0.25 mL corn oil. Dosages are based on toxicity studies described above. Group 5 will be castrated 1 week after LNCaP xenografting as a low androgen control. Each mouse will be treated daily for 2 months. LNCaP tumor growth will be determined twice weekly and tumor volume will be determined. Two months after LNCaP xenografting, mice will be sacrificed and all LNCaP tumors will be removed and fixed in 10% formalin for histological examination by light microscopy. At the time of euthanasia, blood will be collected to determine circulating testosterone, luteinizing hormone, and PMCol levels as performed below. Also, livers and male sexual accessory organs (i.e., seminal vesicles and prostate lobes) will be collected from each mouse for analysis of PMCol's effects on these tissues.

The TRAMP prostate carcinogenesis model will be used to assess the anti-androgenic activity of PMCol on androgen-dependent tumor growth in the mouse prostate using a TRAMP mouse colony maintained on a C57BL/6 background. At 3 months of age, before the onset of prostate carcinogenesis, heterozygous male TRAMP mice will be divided into 5 treatment groups, as described above. Flutamide's efficacy in the TRAMP model has been reported (Raghow et al., Cancer Res. 60: 4093-4097 (2000)). TRAMP mice on study will be treated daily. Four months after the initiation of treatment, at which point approximately 50% of the mice show demonstrable prostatic adenocarcinomas, mice will be sacrificed and the prostate lobes and sex accessory glands will be removed and fixed in 10% formalin and prepared for histological analysis.

Hematoxylin and eosin stained slides of prostate glands will be examined for the presence of prostatic adenocarcinomas, which will be quantified for each treatment group and used to determine the incidence of prostate carcinomas in control versus treatment groups. Blood will also be collected to determine circulating testosterone, luteinizing hormone, and PMCol levels as performed below.

Determining the effect of the vitamin E analog PMCol on central nervous system feedback control of testosterone and luteinizing Hormone blood levels compared to PMCol blood levels will be performed as follows. Four-month-old male ICR mice (Harlan Sprague Dawley) will be used to assay the effect of PMCol administration on blood testosterone levels. Mice will be divided into 5 groups of 5 mice each. Mice in group 1 will receive a vehicle control of 0.25 mL of corn oil by gavage, group 2 will receive 25 mg/kg of flutamide (Sigma) as a treatment control antiandrogen, group 3 will receive 25 mg/kg of PMCol in 0.25 mL corn oil, and group 4 will receive 100 mg/kg of PMCol in 0.25 mL corn oil. Group 5 will be castrated as a low androgen control. Mice 5 will be treated daily for 1 month and blood samples will be collected twice a week by retro-orbital bleed, as previously performed (Church et al., 1999). Blood testosterone levels will be determined using a Testosterone EIA Test Kit (BioCheck, Inc., Burlingame, Calif.). In addition, the testosterone blood levels determined by the EIA kit will be validated using LC-MS. The luteinizing hormone levels in the blood samples will be determined using the Luteinizing EIA Test Kit (BioCheck, Inc., Burlingame, Calif.) according to kit instructions. Finally, PMCol blood levels will be determined from the samples using LC-MS.

It is understood that the examples and embodiments described herein are for illustrative purposes only and that various modifications or changes in light thereof will be suggested to persons skilled in the art and are to be included within the spirit and purview of this, application and scope of the appended claims. All publications, patents, and patent applications cited herein are hereby incorporated by reference in their entirety for all purposes.

What is claimed is:

1. A method of providing nutraceutical benefits to a human patient comprising the step of administering to the patient a nutraceutical composition including:

(a) a compound having the formula:

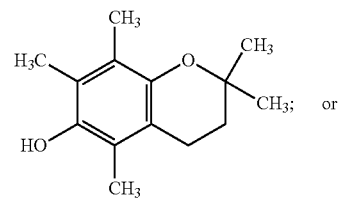 [SMILES: Cc1c(C)c2c(c(C)c1O)CCC(C)(C)O2]

or (b) a pharmaceutically-acceptable salt of said compound; and (c) an acceptable carrier, wherein the nutraceutical benefits comprise treating an androgen-related disorder selected from the group consisting of hirsutism, acne, seborrhea, androgenic alopecia, hyperpilosity, benign prostatic hypertrophy, adenomas or neoplasias of the prostate, benign or malignant tumor cells containing the androgen receptor, osteoporosis, cachexia, endometriosis, polycystic ovary syndrome, male sexual dysfunction, female sexual dysfunction and infertility.

2. The method of claim 1 wherein said nutraceutical composition further comprises an immune boosting agent, anti-inflammatory agent, anti-oxidant agent, or a mixture thereof.

* * * * *